United States Patent [19]

Gentelia et al.

[11] Patent Number: 5,078,677
[45] Date of Patent: Jan. 7, 1992

[54] APPARATUS FOR COLLECTING BLOOD FROM A CHEST DRAINAGE UNIT AND REINFUSION OF THE BLOOD

[75] Inventors: John S. Gentelia, Madison; Stephen J. Roberts, Sauquoit; Frank R. Williams, Utica, all of N.Y.

[73] Assignee: Conmed Corporation, Utica, N.Y.

[21] Appl. No.: 427,958

[22] Filed: Oct. 25, 1989

Related U.S. Application Data

[63] Continuation of Ser. No. 102,480, Sep. 29, 1987, abandoned.

[51] Int. Cl.⁵ ............................................. A61M 37/00
[52] U.S. Cl. ........................................ 604/4; 604/317; 604/319
[58] Field of Search .................... 604/4, 49, 403, 406, 604/317–321; 128/764

[56] References Cited

U.S. PATENT DOCUMENTS

| | | | |
|---|---|---|---|
| 2,999,500 | 9/1961 | Schürer | 604/141 |
| 4,006,745 | 2/1977 | Sorenson et al. | 604/4 |
| 4,014,329 | 3/1977 | Welch et al. | 604/4 |
| 4,346,711 | 8/1982 | Agdanowski | 604/319 |
| 4,372,336 | 2/1983 | Cornell et al. | 604/321 |
| 4,444,548 | 4/1984 | Anderson et al. | 604/317 |
| 4,466,888 | 8/1984 | Verkaart | 604/406 |
| 4,522,623 | 6/1985 | Lauterjung | 604/319 |
| 4,540,413 | 9/1985 | Russo | 604/320 |
| 4,564,359 | 1/1986 | Ruhland | 604/320 |
| 4,650,477 | 3/1987 | Johnson | 604/321 |
| 4,675,010 | 6/1987 | Siposs et al. | 604/319 |
| 4,744,785 | 5/1988 | Rosenthal et al. | 604/320 |
| 4,772,256 | 10/1988 | Lane et al. | 604/4 |

OTHER PUBLICATIONS

"Pleur-Evac Autotransfusion System" brochure 1/86.

Primary Examiner—John D. Yasko
Assistant Examiner—Anthony Gutowski
Attorney, Agent, or Firm—Breiner & Breiner

[57] ABSTRACT

The present invention is directed to a self-contained, totally disposable apparatus for the collection and reinfusion of blood which is suitable for use with a chest drainage unit to provide for the autotransfusion of autologous blood and the method of suing the apparatus. The blood collection and reinfusion apparatus is separate in structure from the chest drainage unit and comprises a rigid outer container and an inner flexible container in conjunction with portals for blood collection, reinfusion, and attachment to a vacuum source. The apparatus and method of the invention provides a closed system, requires minimal handling of the blood, and provides for greater patient safety in that no interruption of the operation of the chest drainage unit is required.

2 Claims, 3 Drawing Sheets

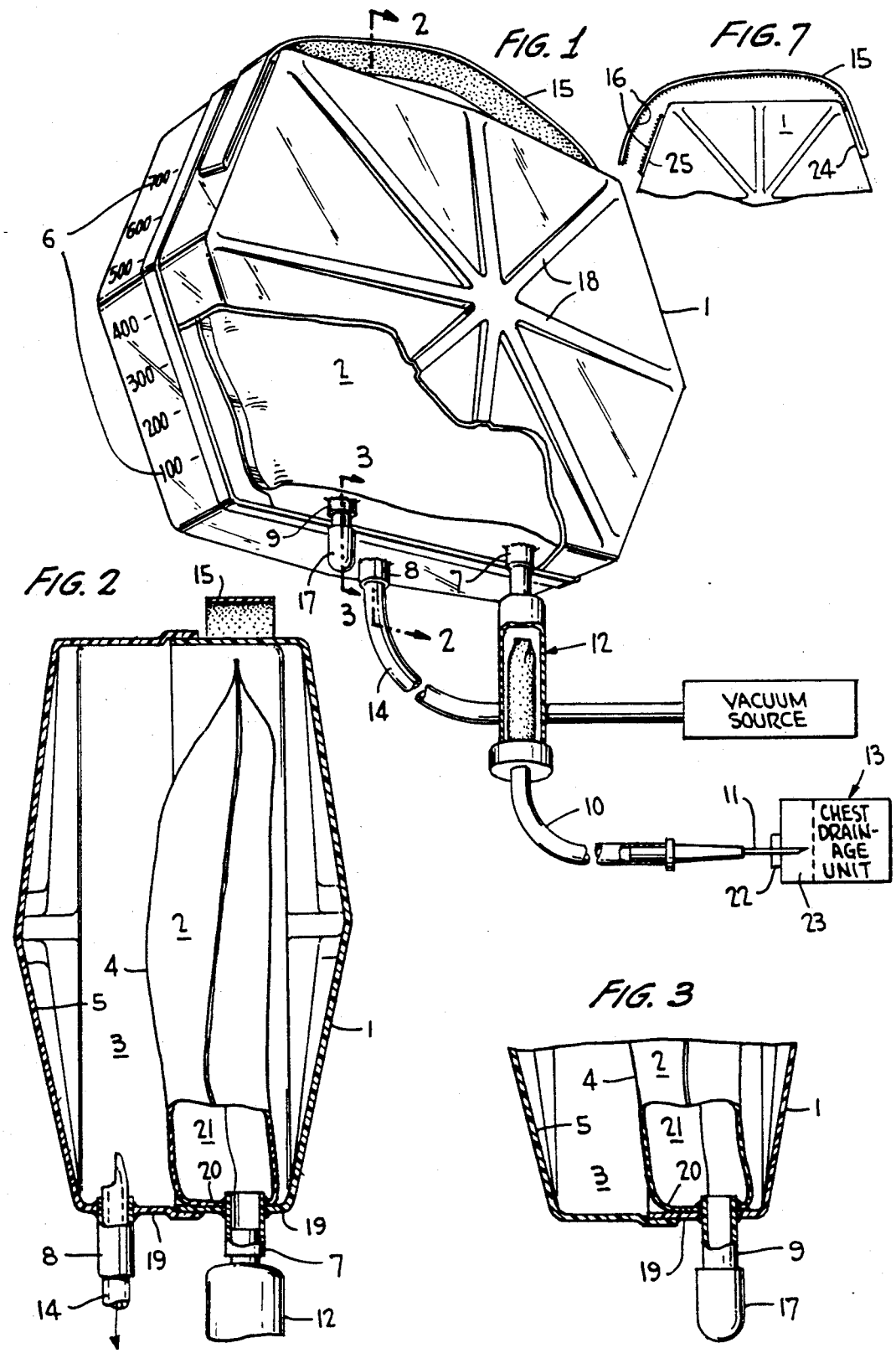

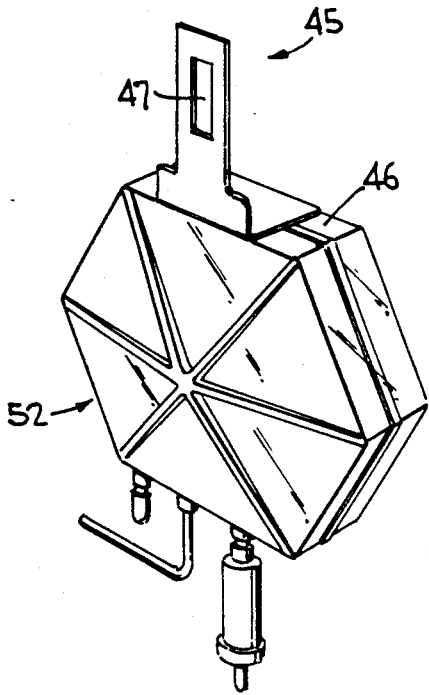
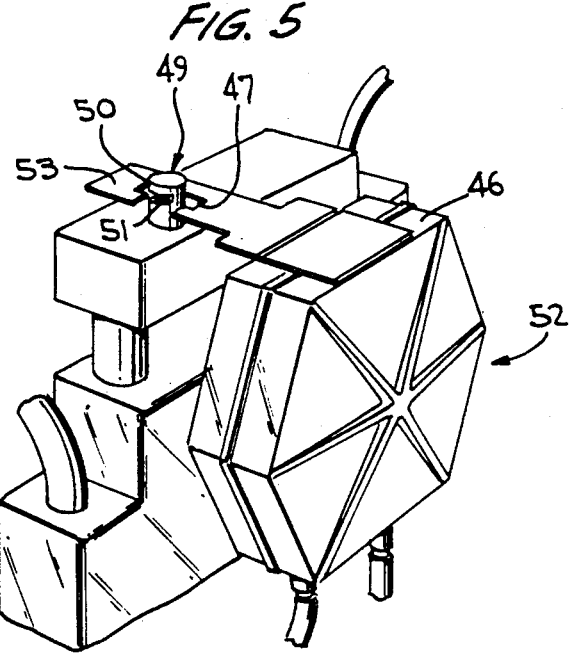
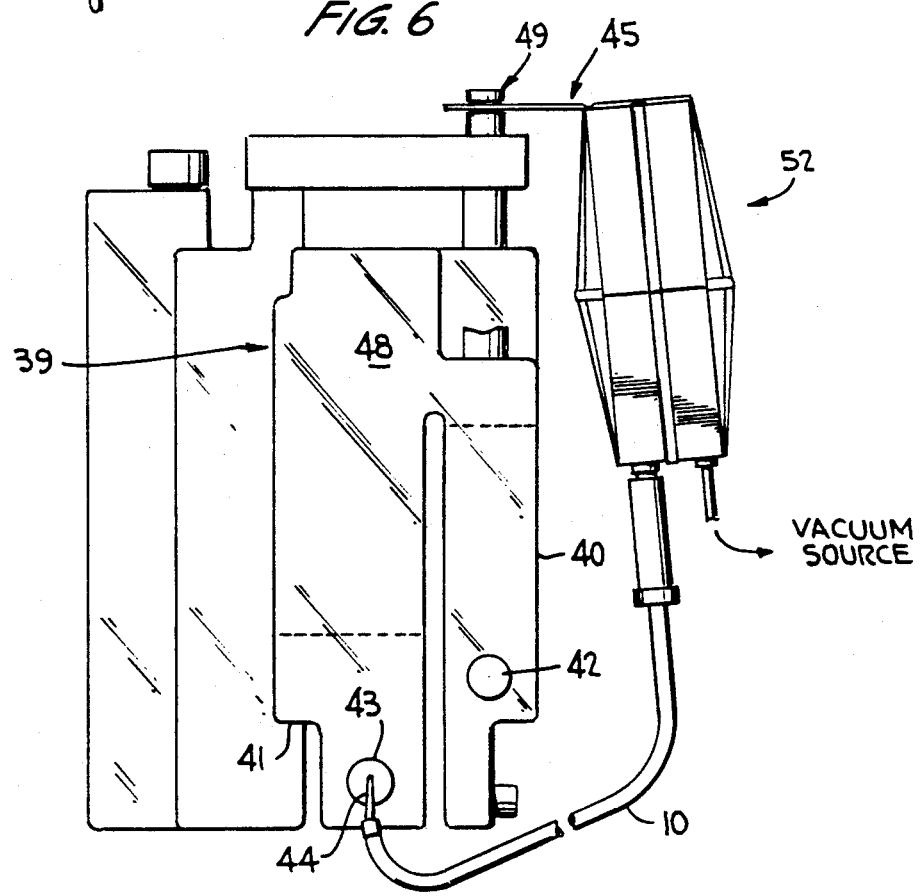

APPARATUS FOR COLLECTING BLOOD FROM A CHEST DRAINAGE UNIT AND REINFUSION OF THE BLOOD

This is a continuation of application Ser. No. 102,480, filed Sept. 29, 1987, abandoned.

FIELD OF INVENTION

The present invention is directed to a method and apparatus for the collection of blood from a chest drainage unit and the reinfusion of the collected blood into a patient. More specifically, the present invention is directed to a self-contained, totally disposable apparatus suitable for collecting blood from a chest drainage unit and reinfusing the collected blood having a rigid outer container, an inner flexible container, collection and reinfusion portals, and means for attachment to a vacuum source.

BACKGROUND OF INVENTION

Autotransfusion refers to the reinfusion of a medical patient's own blood. Homologous infusion refers to a blood transfusion where the blood is collected from a donor and transfused to a compatible patient. Autotransfusion is preferred since no testing of the blood is required because the blood transfused is that of the patient and further, since the patient will not be subjected to the possibility of a blood carried disease, such as hepatitis, AIDS, etc. Additionally, autotransfused blood is more fresh than "banked blood" and contains the patient's own antibodies.

Autotransfusion is categorized into three categories. First, "pre-operative" where the patient donates his or her own blood prior to scheduled surgery and the blood is stored for that patient's later use. Second, "intra-operative" when during the course of surgery, the shed blood is collected, filtered, washed, and reinfused back into the patient. Thirdly, "post-operative" where following surgery, blood drainage is collected and reinfused into the patient. Post-operative autotransfusion is limited in use since there are strict criteria for the type of blood which can be reinfused. Currently, the only post-operative blood believed suitable for autotransfusion is mediastinal blood, i.e. the blood which comes from the anatomical space or cavity in the chest where the heart is located.

Underwater chest drainage units are presently used in the post-operative care of patients having surgery involving entry into the chest. Chest drainage units are also used in trauma cases and certain medical applications which require the removal of fluids and air from inside the chest cavity. The chest drainage unit removes fluid or air from a chest cavity by the use of catheters placed in the chest cavity at the end of surgery. The chest drainage unit is connected to a vacuum source which applies a suction to the chest tubes to remove the drainage and trapped air from within the patient.

The use of an autotransfusion unit in combination with a chest drainage unit is known in the art. For example, U.S. Pat. No. 4,445,884 discloses an autotransfusion unit for collecting blood and purZging air from the collected blood attached to an underwater drainage system, such as a chest drainage system. The unit disclosed in the '884 patent, however, while connected to a drainage system, collects blood directly from the patient through an inlet tube attached to the tubing aspirating blood from the patient to the drainage system. The autotransfusion unit disclosed in the '884 patent is connected to the drainage system for the purpose of maintaining the negative pressure on the collection chamber of the unit due to a suction source attached to the drainage system and for the purpose of drawing out the air purged from the blood in the collection chamber. Once the blood is purged of air, the blood is taken from the collection chamber and reinfused into the patient. Clamps are used to control the flow of blood, purged air, and vacuum pressure of the chamber. The structure of the collection chamber discussed in the '884 patent is more fully disclosed in U.S. Pat. No. 4,424,053 which is referred to in the '884 patent by Ser. No. 290,666, filed Aug. 5, 1981. U.S. Pat. No. 4,540,413 discloses a cardiopulmonary drainage collector having a blood transfer adaptor. The '413 patent is directed to the structure of a drainage collector which has a chamber for collecting blood from a patient. The patent discloses that the blood collected in the chamber can be removed from the chamber by a blood transfer needle connecting tube which punctures a seal in the chamber. The connecting tube is attached to a standard blood bag used for collecting transferred blood. Once the blood bag is filled, it can be processed for reinfusion.

Two specific systems currently on the market which incorporate autotransfusion with chest drainage are the Sorenson "RECEPTAL" and Deknatel's "Pleur-Evac ATS". The Sorenson product utilizes a plastic bag which is placed inside the collection chamber of a chest drainage unit. The bag is in a negative pressure container and collects the blood drainage coming into the collection chamber. When the bag is filled, the bag is removed from the negative pressure container and connected to a reinfusion system. During the removal of the blood collection bag and container, however, the connecting tubes are clamped off and the patient is temporarily disconnected from the chest drainage unit and the negative pressure which is required to hold the chest cavity at proper breathing levels. The changeover requires numerous steps which are difficult and time consuming to accomplish. The Deknatel product utilizes an autotransfusion collecting bag in the tubing which is part of the chest tubes connecting the patient's chest to the chest drainage unit. This technique involves an "open" system, i.e. during the disconnection of the blood collecting bag, the blood is exposed to the ambient atmosphere. As with the Sorenson product, the tubes joining the patient's chest cavity to the chest drainage unit must be clamped off during the changeover process.

Further, blood collection units of various structures are known in the art. For example, U.S. Pat. No. 4,573,992 discloses an apparatus for aspirating and reinfusing blood under pressure which in one embodiment comprises a rigid container enclosing a deformable inner container having a space between the outer container's inner walls and the inner container's outer walls. The deformable and rigid containers are connected to a suction line which aspirates blood into the inner container through an aspirator tube which is connected to another portal in the apparatus. The inner deformable container does not collapse during collection of blood due to the pressure in the space existing between the outer rigid container and the inner container. The pressure is applied from a pressure source which is attached to the rigid container at a side portal which pressurizes the space between the outer and inner containers. A plug can be inserted into the pressure connection portal to maintain the pressure in the space between the containers. When the collection of blood is completed, the inlet which is connected to the suction source is disconnected and the collection unit is then connected to an infusion set so that the collected blood can be reinfused into the patient. Additionally during reinfusion of the blood, the inlet connected to the pressure source is opened so that a controlled feed of pressure medium enters the space between the outer rigid container and the deformable inner container thereby applying pressure to the outside of the inner container causing the blood in the inner container to be fed through the infusion set. The patent does not disclose connecting the apparatus to a drainage system. U.S. Pat. No. 4,402,687 discloses a suction collection system for collecting blood from a patient for reinfusion into the patient. The collection system comprises a rigid hollow canister having a thin flexible plastic sheet material covering the entire outer surface of the canister to form an airtight receptacle. The apparatus contains a first portal in the top wall of the canister which is connected to a vacuum source for reducing the pressure within the receptacle. A second portal in the canister is connected to an aspirator for collecting blood and other body fluids from a patient. Fluid within the receptacle is removed through a normally closed outlet port in the bottom of the canister. An air inlet port is also contained in the top surface of the canister. It is further disclosed that rather than using an aspirator, a chest tube or other similar drainage device can be utilized. U.S. Pat. No. 4,564,359 discloses an autotransfusion unit for collecting blood to be used for retransfusion. The autotransfusion unit contains a bottom inlet attached to a vacuum source for drawing blood into the collection chamber, an upper inlet through which the blood enters the collection chamber, and an upper outlet through which the blood exits the collection chamber when the autotransfusion unit has been disconnected from the patient and inverted. The collection chamber of the autotransfusion unit is divided into two portions a bottom gas filled space which is separated from an upper portion which receives the collected blood.

The art does not disclose a blood collection and reinfusion unit having the combined structure of the present invention used in conjunction with a chest drainage unit for the autotransfusion of blood in accordance with the method of the present invention.

OBJECTS OF INVENTION

A primary object of the present invention is to provide a sterile, self-contained, totally disposable apparatus for the collection and reinfusion of blood for use with a chest drainage unit.

A further primary object of the present invention is to provide a method of collecting blood from a chest drainage unit utilizing a sterile, self-contained, totally disposable apparatus for collecting and reinfusing blood.

A further primary object of the present invention is to provide a method of autotransfusion utilizing a sterile, self-contained, totally disposable apparatus for the collecting and reinfusing of blood which is utilized with a chest drainage unit.

A further object of the present invention is to provide a method and apparatus such as stated above, which provides the following advantages:

(1) A closed system, i.e. during the transfer process the blood is not exposed to the ambient air, other patients or hospital staff thereby eliminating airborne contamination and cross-infection;

(2) Requires less handling of the blood, i.e. involves fewer steps in the transfer, collection, and reinfusion process which means less potential for the contamination of the blood or cross-infection to staff or other patients;

(3) Provides for greater patient safety, i.e. no clamping off of tubes or other interruption of the operation of the chest drainage unit is required during collection or removal of the blood so that the patient is not cut off from the vacuum source which keeps the chest cavity at a negative pressure and provides drainage of the fluids and trapped air from the chest cavity; and (4) The autotranfusion unit is cost effective because it is not an integral part of the chest drainage unit, i.e. the autotranfusion unit is only utilized where the patient will actually receive the blood (In drainage units where the autotransfusion unit is an integral part of the chest drainage unit, the expense is incurred each time the chest drainage unit is utilized regardless whether the patient requires blood. Many factors can disqualify blood from autotranfusion and further, in many cases the patient's bleeding is not sufficient to require reinfusion of the blood in which instance the blood is disposed of by the hospital. Studies show that of the total number of potential patients for autotransfusion, only 20% actually receive transfused blood.)

BRIEF DESCRIPTION OF INVENTION

The structure of the apparatus for the collection and reinfusion of blood of the present invention comprises a rigid outer container having an inner flexible container with a space existing between the flexible container's outer walls and the rigid container's inner walls. A negative pressure is maintained in the space between the inner and outer containers which causes the inner flexible container to expand and draw in blood during the collection of blood, such as from a chest drainage unit. In one embodiment, the rigid container has two portals which extend through the walls of the rigid and flexible containers and into the interior of the inner container and one portal extending through the wall of the rigid container and entering the space existing between the inner walls of the rigid container and the outer walls of the flexible inner container. The first portal passing through the outer container wall into the inner container is a collection portal, i.e. an inlet for a tube or the like which is to be attached to a chest drainage unit and which preferably has an inline filter. The second portal passing through the outer container wall into the inner container serves as a reinfusion portal. The third portal passing through the outer container wall and not into the inner container serves as an inlet for a vacuum source and is utilized during the collection of blood from a chest drainage unit. During the collection of blood from the chest drainage unit, the collection and reinfusion apparatus is connected to the chest drainage unit by tubing attached to the collection portal which has a surgical needle on its extended end. The surgical needle is inserted into a self-sealing diaphragm in the wall of the blood collection chamber of the chest drainage unit. As stated above, the collection and reinfusion apparatus is also connected to a vacuum source during the collection of blood which serves to draw the blood from the collection chamber in the chest drainage unit into the inner flexible container of the collection and reinfusion apparatus. When the transfer of blood is complete, the collection and reinfusion apparatus is disconnected from the chest drainage unit without interrupting the operation of the chest drainage unit and is thereafter ready to be connected to a conventional infusion set and suspended from a suitable suspension means in the vicinity of the patient to reinfuse the collected blood into the patient.

In an alternative embodiment of the blood collection and reinfusion apparatus, the apparatus has only two portals, i.e. one portal for the collection and reinfusion of the blood and one portal for connection to a vacuum source. The collection/reinfusion portal extends through the wall of the outer and inner containers so that one end of the portal is located in the interior of the inner container. The vacuum portal extends through the wall of the outer container into the space existing between the inner walls of the outer container and the outer walls of the inner container. Blood is collected through the collection/reinfusion portal by use of a tube with a needle attached to its free end preferably having an inline filter wherein the needle is inserted into a self sealing diaphragm located in the wall of the chest drainage unit's blood collection chamber. When the apparatus is sufficiently filled with blood, the collection portal is clamped off and the collection tube is removed from the diaphragm of the chest drainage unit. Thereafter, the collection tube is removed from the collection/reinfusion portal and a conventional infusion set is attached to the portal. Reinfusion of the collected blood is accomplished by suspending the collection and reinfusion apparatus above a patient by a suitable suspension means and removing the clamp closing off the portal to allow blood to flow from the apparatus through the infusion set to the patient. The vacuum source is removed from the second portal prior to reinfusion.

BRIEF DESCRIPTION OF DRAWINGS

FIG. 1 sets forth a perspective view of one embodiment of the apparatus for collecting and reinfusing blood and connection thereof to a chest drainage unit.

FIG. 2 sets forth a cross-sectional view along line 2—2 of FIG. 1.

FIG. 3 sets forth a cross-sectional detailed view along line 3—3 of FIG. 1.

FIG. 4 sets forth a preferred embodiment of a suspension means for the collection and reinfusion apparatus.

FIG. 5 sets forth the suspension means shown in FIG. 4 attached to a chest drainage unit.

FIG. 6 sets forth a chest drainage unit showing the blood collection chambers and blood sampling ports which are a part of the chest drainage unit.

FIG. 7 sets forth a detailed view of an alternative means of suspension for the blood collection and reinfusion apparatus.

DETAILED DESCRIPTION AND PRESENTLY PREFERRED EMBODIMENT OF INVENTION

Figure 8:
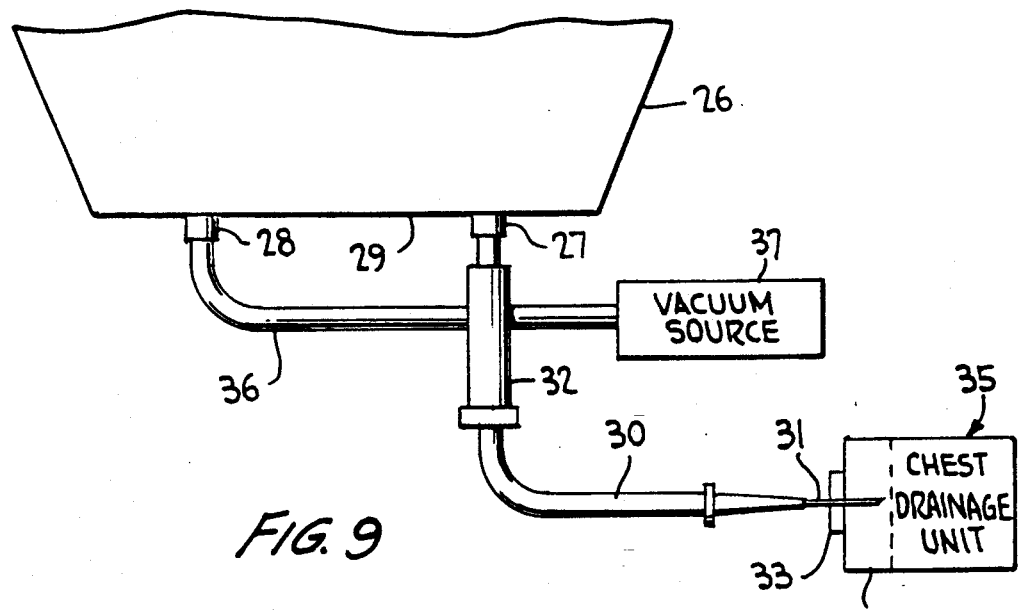
FIG. 8 sets forth a second embodiment of the apparatus for collecting and reinfusing blood showing the vacuum connection tube and blood collection tube connected to the apparatus.

The blood collection and reinfusion apparatus of the present invention is particularly suitable for use with a chest drainage unit. Chest drainage units are used in the post-operative care and treatment of a medical patient. The apparatus and method of the present invention provides for the autotransfusisn of blood, i.e. the reinfusion of a patient's own blood, without the necessity of collecting the patient's blood directly from the patient or interrupting the operation of the chest drainage unit subsequent to the unit's connection to a patient. The apparatus and method of the invention allows for the collection of blood directly from a chest drainage unit. The same apparatus used for collecting the blood is then used for the reinfusion of the collected blood directly into the patient without any further transfer of the blood. Accordingly, the apparatus and method of the invention allows for the sterile, efficient, and cost effective collection and reinfusion of autologous blood.

For the purpose of discussion, the apparatus for collecting and reinfusing blood of the present invention will be referred to as an autotranfusion unit.

The autotranfusion unit of the present invention is a sterile, self-contained, totally disposable apparatus useful in the collection of autologous blood from a chest drainage unit and the reinfusion of the collected blood into the patient.

The autotransfusion unit of the invention can be utilized with any suitable chest drainage unit and is not an integral part of the chest drainage unit's structure. The only structural requirements that the chest drainage unit must meet are that the portions of the unit coming into contact with the blood be made of a material which is biocompatible with blood (which is a common feature of chest drainage units which collect blood which requires testing or will be used for blood transfusions) and have a means of access into the chest drainage unit's blood collection chamber, such as a self-sealing diaphragm in the wall of the collection chamber. Blood sampling ports, such as are used to draw out samples of blood so that the collected blood can be tested, utilize a self-sealing diaphragm. Blood sampling ports usually are made utilizing a self-sealing rubber diaphragm. The self-sealing diaphragm is the site at which the autotransfusion unit of the invention is connected to the chest drainage unit during collection of blood from the chest drainage unit. The means and method of connection will be more fully discussed below.

An example of a suitable chest drainage unit is known as the PLEURA-GARD ™ underwater chest drainage unit which is manufactured by Conmed Corporation of Utica, New York. The PLEURA-GARD ™ chest drainage unit is made of a plastic resin which is compatible for blood contact service, i.e. the plastic resin does not negatively react with the blood or cause any destruction of the blood cells. As shown in FIG. 6, the PLEURA-GARD ™ unit incorporates a 2500 ml collection chamber 39 for receiving drainage. The collection chamber is divided into two subchambers. The first subchamber 40 has a capacity of 450(+)ml. When the first subchamber is filled, the collected blood is forced by the incoming blood to overflow into a second subchamber 41. Each subchamber 40 and 41 has a port, 42 and 43 respectively, located in the subchamber's sidewall. These ports each have a self-sealing diaphragm and are used for removing blood samples from the collection subchambers. The blood sampling ports are located sufficiently above the bottom edge of each subchamber's sidewall to eliminate blood clots which have settled to the bottom of the blood collection subchambers from entering and plugging a needle 44 which is inserted into the ports to collect blood. The blood is unaffected by a transfer through these ports. A fuller description of the transfer of the blood through these ports using a blood collection tube 10 which is attached to an autotransfusion unit 52 will be set forth below in conjunction with the description of the autotranfusion unit and its use.

The preferred embodiment of the autotranfusion unit of the present invention comprises a rigid outer container 1 having an inner flexible container 2 with a space 3 existing between the flexible container outer walls 4 and the rigid container's inner walls 5. The outer or inner container can be marked with a suitable volume indicating means, such as a scale 6, to allow a direct reading of the collected fluid. The volume indicator can reflect any suitable measurement. The preferred capacity of the inner flexible container is 700 ml and accordingly, the volume indicator will preferably read to a capacity of 700 ml.

The size and strength of the rigid outer container, such as determined by the container's wall thickness and material used in making the container, is sufficient to enclose and support a fluid material containing expanded inner container. The outer container is preferably made of a transparent plastic material which is rigid in its final form. The walls of the rigid outer container can have support ribs 18 or the like as an integral part thereof to provide supporting strength to the container structure. Since the outer container does not come into contact with the collected blood, any conventional plastic suitable for forming a rigid container is acceptable for use. Examples of suitable materials for making the outer rigid container include, but are not limited to, polyethylene, polyurethane, polyamide or the like.

The inner flexible container is preferably a collapsible bag or pouch-like member made of a blood biocompatible material, preferably a plastic. Examples of suitable materials for making the inner flexible container include, but are not limited to, polyethylene, silicone rubber, polyvinylchloride, polyurethane or the like.

In one embodiment of the present invention, the autotransfusion unit has three portals, denoted in FIGS. 1, 2, and 3 as 7, 8, and 9. The portals have one end extending into the interior of the outer rigid casing and/or inner flexible casing as shown in the drawings and as will be more fully described below, and one end extending externally of the outer rigid container. The first portal, denoted as 7, is the collection portal. The collection portal 7 extends through the rigid outer container wall 19 and the flexible inner container wall 20 to provide a passage into the interior 21 of the inner flexible container, such as shown in FIG. 2. The inner flexible container 2 is sealed by a conventional sealing means, i.e. adhesive, heat seal, etc., around portal 7 so as to provide a leakproof seal. A length of tubing 10 having a needle 11 attached at its free end is attached to collection portal 7. Tube 10 preferably has an inline high aggregate filter 12. The filter is provided to remove clots from the blood being collected. The needle is preferably a 14 gauge surgical needle. Needle 11 on the free end of the tube 10 is inserted into a self-sealing diaphragm 22, after the diaphragm has been properly cleaned with an antiseptic, located in the wall of the blood collection chamber 23 of the chest drainage unit 13. The second portal 8 of the autotransfusion unit extends through wall 19 of the outer rigid container into the space 3 existing between the flexible container's outer wall 4 and the rigid container's inner wall 5. Attached to second portal 8 is a length of tubing 14 which is connected to a suitable vacuum source. The vacuum source applies negative pressure through portal 8 to space 3 which causes the inner flexible container 2 to expand and draw blood from the chest drainage unit blood collection chamber 23 into the inner flexible container 2 through collection portal 7. On the completion of the collection of the blood from the chest drainage unit, the autotranfusion unit is properly sealed, such as by the use of tube clamps attached to the blood collection tube 10 (not shown). The autotranfusion unit is then aseptically disconnected from the chest drainage unit and vacuum source whereby the inner flexible container collapses around the collected blood. Reinfusion of the collected blood from the autotransfusion unit into the patient is then possible.

To reinfuse the collected blood into the patient, a conventional infusion set such as known in the art is attached to portal 9. Portal 9, as shown in FIG. 3, extends through wall 19 of the outer rigid container 1 and wall 20 of the inner flexible container 2 into the interior 21 of the inner container 2. As with portal 7, the inner flexible container 2 is sealed by a conventional sealing means around portal 9 so as to provide a leakproof seal. During the collection of fluid into the autotranfusion unit through portal 7, cover 17 is positioned over portal 9 to maintain the sterility of the unit. When the infusion set is ready to be attached to portal 9, cover 17 is removed and an infusion set is aseptically connected to portal 9. A suitable infusion set for use in the reinfusion of collected blood consists of a connecting tube, a filter and a surgical needle attached to the free end of the tube. The filter can be between 40–170 microns depending on a doctor's specification. The surgical needle is preferably a 15 gauge surgical needle. The infusion connecting tube is attached to portal 9. The needle is inserted into the patient. When the vacuum source is removed from portal 8, the inner flexible container 2 collapses as stated above and the blood therein is free to flow through portal 9 and the infusion see into the patient.

During collection of blood from the chest drainage unit and the reinfusion of the collected blood into the patient, the autotranfusion unit is hung from a suitable suspension means. The suspension means can be formed as an integral part of the autotransfusion unit's rigid outer container or be a separate structure which is attached to the autotransfusion unit's outer rigid container by any conventional means, such as an adhesive.

The preferred suspension means, shown in FIG. 4, comprises a semi-rigid member or tab 45 extending from the top surface of the outer rigid container 46 of the autotransfusion unit 52. The tab or extension 45 has an opening 47 contained in the approximate center of the extension. The semi-rigid member is preferably made of plastic. In relation to the tab structure, semi-rigid is to be understood as providing sufficient strength to the tab structure s that the structure does not collapse around the tab's center opening when the autotransfusion unit is suspended from the tab, but at the same time has sufficient flexibility to allow the tab to bend at a sideways angle, such as shown in FIG. 5. The tab's flexibility allows adjustability of the autotransfusion unit's position in relation to the structure from which the autotransfusion unit is hung.

The blood collection chamber of chest drainage units have a cavity located in the upper interior area of the chamber. To relieve the build up of negative pressure within the collection chamber, chest drainage units, such as the PLEURA-GARD ™ chest drainage unit described above and shown in FIG. 5, have a negative pressure relief valve structure 49. When the button of the valve structure is depressed, the collection chamber is vented, i.e. any build up of negative pressure within the chamber is relieved. A filter is present in conjunction with the valve's structure to avoid any contamination of the blood contained in the collection chamber. The negative pressure relief valve structure has a circular wall 50 positioned around the valve's button. The button is normally required to be depressed manually. The wall 50 protects the button from being accidentally depressed. As shown in FIG. 5, the protective wall 50 can be formed with a half-ring or slice 51 cut into the wall 50. This slice 51 is used to maintain the relief button in a depressed position. The suspension means, such as described above and shown in FIG. 4, can be used in conjunction with the relief button's protective wall 50, shown in FIG. 5, to allow the autotransfusion unit to maintain the negative relief valve button in a depressed position and thereby continually vent the blood collection chamber during collection of blood therefrom.

As shown in FIG. 5, the autotransfusion unit 52 can be suspended from the chest drainage unit by positioning the center opening 47 of the suspension means 45 around the protective wall 50 of the relief button. The flattened wall portion 53 of the suspension means fits in the slice 51 in the protective wall 50 of the valve structure. The weight of the autotransfusion unit then serves to pull against the relief valve's protective wall 50. Due to the resiliency of the protective wall (which can be due to the material from which the wall is made or a spring within the valve structure) the wall is pulled to one side by the weight of the autotransfusion unit causing the protective wall to wedge against the valve's button and depress the button. This method of suspension provides for a continual means of venting the blood collection chamber during blood collection thereby avoiding the need of a person to monitor and physically depress the relief button. This method of suspension frees the time of a patient's attendant to tend to other matters.

During reinfusion the same suspension means as described above can be used to hang the autotranfusion unit from an I.V. pole or the like which is positioned in the vicinity of the patient.

An alternative suspension means can be any conventional means such as a hook-like member or strap. While this alternative means can not be utilized in conjunction with a negative relief valve structure such as described above, it does allow the autotransfusion unit to effectively operate to collect blood from a chest drainage unit and reinfuse blood into a patient. The monitoring of the negative pressure in the blood collection chamber and the relief thereof would then be carried out in a conventional manner.

The hook-like member of the alternative suspension means can be formed as an integral part of the rigid outer container or can be a separate member secured to the rigid outer container by a suitable means such as an adhesive. The preferred alternative suspension means is a strap such as shown in FIG. 7. The strap comprises a fabric or plastic strip 15 which is permanently attached at one end of the strip to one side 24 of the rigid outer container 1 by a suitable means, such as an adhesive, and is removably attached at its other end to the opposite side 25 of the rigid container, such as by interlocking loops and hooks 16 which is known by the name VELCRO ™. The use of a removable fastener such as VELCRO ™ on one end of the suspension means allows for adjustment of the suspension means and ease in attachment of the autotransfusion unit to another structure.

The collection and reinfusion portals which are part of the autotranfusion unit structure are cylindrical, tubelike sections made from a plastic which is biocompatible with blood. The portals are inserted into openings in walls 19 and 20 of the outer and inner containers and secured therein by any suitable conventional means, i.e. by an adhesive, heat sealing, etc. Additionally, the collection, reinfusion, and vacuum portals can be formed as an integral part of the outer rigid container 1. The inner flexible container will then be secured to the inwardly projecting portion of the collection and reinfusion portals. If the portals are an integral part of the outer container, the plastic or other material utilized to make the container must be blood compatible since the blood will come into contact with the interior of the collection and reinfusion portals. An alternative to making the whole outer rigid container of a blood biocompatible material, would be to line the blood contacting portion of the portals with a blood compatible material. It is noted that whichever form is utilized, the inner flexible container 2 is secured around portals 7 and 9 in such a manner that leakage from the inner container or the contamination of the interior of the inner container by any airborne matter is not possible.

Figure 9:
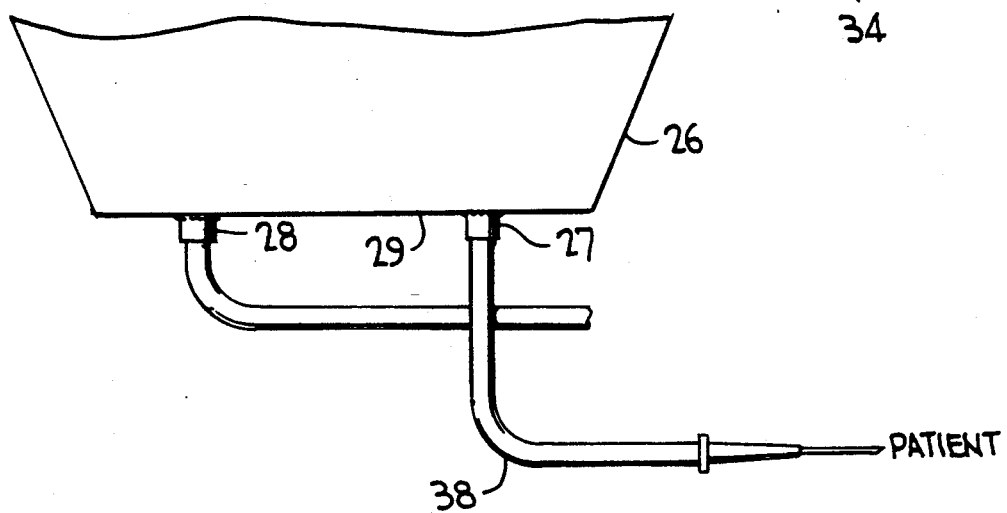
FIG. 9 sets forth a second embodiment of the apparatus for collecting and reinfusing blood with an infusion set connected thereto.

In an alternative embodiment, shown in FIGS. 8 and 9, the autotranfusion unit is comprised of a rigid outer container 26 enclosing an inner flexible container as described above. The interior arrangement and portal structure of the alternative embodiment is the same a described above with respect to the first embodiment and accordingly, is not discussed or shown in detail with respect to the alternative embodiment. Rather than having three portals, however, the autotransfusion unit of the alternative embodiment has two portals 27 and 28. Portal 27 is used for blood collection and reinfusion. Portal 28 is connected to a vacuum source in the same manner a described above with respect to portal 8 of the first embodiment.

FIG. 8 shows the arrangement of attachments to portals 27 and 28 during collection of blood from a chest drainage unit. Portal 27 extends through wall 29 of the outer rigid container 26 and the wall of the inner flexible container into the interior of the inner flexible container as shown in FIG. 2 with respect to portal 7. Portal 28 extends through wall 29 of the rigid outer container into the space existing between the flexible container's outer wall and the outer container's inner wall as shown in FIG. 2 with respect to portal 8. Collection/reinfusion portal 27 has connected thereto during collection of blood from the chess drainage unit a specified length of tubing 30 with a needle 31 at its free end. Preferably, tubing 30 has a high aggregate inline filter 32 for blood clot removal. Needle 31 at the end of tubing 30 is inserted into a self-sealing diaphragm 33 in the wall of the blood collection chamber 34 of the chest drainage unit 35 such as described above with respect to the first embodiment for the collection of blood from the chest drainage unit. Portal 28 has a tube 36 attached thereto which is connected to a vacuum source 37 at its free end. Negative pressure is applied through portal 28 to the interior space of the outer rigid container surrounding the inner flexible container causing the inner flexible container to expand and draw blood into the inner container from the chest drainage unit as described above with respect to the first embodiment. On the completion of the blood collection, tube clamps are utilized to clamp off both the collection and vacuum tubes. The tube clamp attached to the collection tube must be at a point above the area of disconnection of the collection tube since the collection tube will be removed from attachment to portal 27 and an infusion set attached thereafter to portal 27. This technique will maintain a closed system with respect to the collected blood.

Reinfusion of the collected blood is accomplished by suspending the autotranfusion unit in the vicinity of the patient by a suitable suspension means from an I.V. pole or the like. As shown in FIG. 9, a conventional infusion set 38, such as described above with respect to the first embodiment, is attached to portal 27 in the manner described above with respect to portal 9 in the first embodiment, and the vacuum source disconnected from portal 28. When the tube clamps are unclamped from portals 27 and 28, a positive pressure is induced through portal 28 causing the inner flexible container to collapse and start the flow of blood through portal 27 and the attached infusion set 38 to the patient.

As an alternative to attaching the vacuum portal, 8 or 28, to an independent vacuum source, a self-contained vacuum source (not shown) can be made as an integral part of the rigid outer container of the autotransfusion unit. The vacuum source will be of a conventional structure known to one skilled in the art and have power capable of delivering a vacuum which is sufficient to accommodate blood collection from a chest drainage unit such as described above. The vacuum source can be either AC, DC, or manually powered. Additionally, the vacuum source can be secured to the outer rigid container by any suitable means, held within the outer rigid container, fit within a specific pre-molded section of the container or the like.

As will be apparent to one skilled in the art, various modifications can be made within the scope of the aforesaid description. Such modifications being within the ability of one skilled in the art form a part of the present invention and are embraced by the appended claims.

We claim:

1. An apparatus for the collection of blood directly from a chest drainage unit which is attached to a patient, said apparatus permitting subsequent reinfusion of the collected blood directly into a patient, comprising a self-contained unit having a unitary outer rigid container enclosing an inner flexible container; said unit having three portals as an integral part of said outer rigid container each having first and second ends; a first of said portals extending through a wall of said outer rigid container and through a wall of said inner flexible container with one end of said first portal extending into the interior of said inner flexible container with said inner flexible container being sealingly attached to said portal, and said inner flexible container thereby being fixedly connected to said outer rigid container, and the other end of said first portal extending externally of said outer rigid container and having a tube attached thereto, said tube having a needle attached to its free end; a second of said portals extending through a wall of said outer rigid container and through a wall of said inner flexible container with one end of said second portal extending into the interior of said inner flexible container with said inner flexible container being sealingly attached to said portal and the other end of said second portal extending externally of said outer rigid container and being attached to a blood infusion means; a third of said portals extending through a wall of said outer rigid container having one end extending into a space between the inner walls of said outer rigid container and the outer walls of said flexible inner container and the other end extending externally of said outer rigid container and having a tube attached thereto of attachment to a vacuum source.

2. An apparatus for the collection of blood directly from a chest drainage unit which is attached to a patient, said apparatus permitting subsequent reinfusion of the collected blood directly into a patient, comprising a self-contained unit having an outer rigid container enclosing an inner flexible container; said unit having at least two portals each having first and second ends, at least one of said portals extending through a wall of said outer rigid container and through a wall of said inner flexible container so that said first end of said portal extends into the interior of said inner flexible container; said inner flexible container being sealingly attached to said first end of said portal, and said second end of said portal extends externally of said outer rigid container; said second end being constructed and arranged for attachment to a tubular member; a second of said at least two portals extending through a wall of said outer rigid container so that said first end of said second portal extends into a space between the inner wall of said outer rigid container and the outer wall of said inner flexible container, the second end of said second portal extends external of said rigid container and being constructed and arranged for attachment to a vacuum source; and a blood collection tube having a needle fixed to its free end attached to the second end of said first portal; wherein said apparatus is used in combination with a chest drainage unit which has a self-sealing diaphragm located in a wall of said chest drainage unit structured to receive a needle and said needle of the free end of said blood collection tube being inserted into said diaphragm, and said apparatus being attached to said chest drainage unit through an attachment means which comprises a semi-rigid plastic tab extending from the top surface of said outer rigid container of said apparatus having an opening which is attached to said drainage unit which has a manually operable negative relief valve protruding from an upper surface of said chest drainage unit from which said tab is hung so that said negative relief valve is opened.

* * * * *